United States Patent [19]

Shoher et al.

[11] Patent Number: 4,861,267
[45] Date of Patent: Aug. 29, 1989

[54] SLITTED METAL FOIL FOR FORMING A DENTAL COPING AND METHOD

[76] Inventors: Itzhak Shoher, 50 Shlomo-Hamelech St., Tel-Aviv, Israel, 64386; Aharon E. Whiteman, 13 J. L. Perez St., Petach-Tikvah, Israel, 49206

[21] Appl. No.: 93,772

[22] Filed: Sep. 8, 1987

[51] Int. Cl.$^4$ ................................. A61C 5/08
[52] U.S. Cl. ................ 433/218; 433/222.1; 433/223
[58] Field of Search ............ 433/222, 223, 227, 218, 433/207, 208

[56] References Cited

U.S. PATENT DOCUMENTS 4,273,580  6/1981  Shoher et al. ............... 433/207
4,427,501  1/1984  Rogers ....................... 433/199.1
4,459,112  7/1984  Shoher et al. ............... 433/218
4,492,579  1/1985  Shoher et al. ............... 433/222.1
4,676,751  6/1987  Shoher et al. ............... 433/222.1
4,698,021  10/1987  Shoher et al. ............... 433/222.1

Primary Examiner—John J. Wilson
Assistant Examiner—Adriene J. Lepiane
Attorney, Agent, or Firm—E. Lieberstein

[57] ABSTRACT

A slitted metal foil and method for forming a dental coping comprised of a composite body formed from at least two layers of precious metal with at least one or more slits extending from the perimeter to a location at or relatively close to the center of the foil to form slitted ends adapted to be overlaid to form a coping having a conical or frusto-conical shape.

9 Claims, 2 Drawing Sheets

U.S. Patent  Aug. 29, 1989  Sheet 2 of 2  4,861,267
FIG. 6
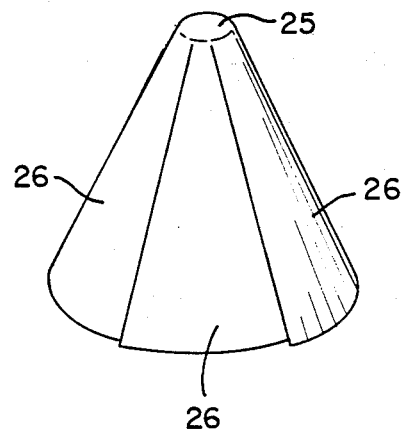
FIG. 7
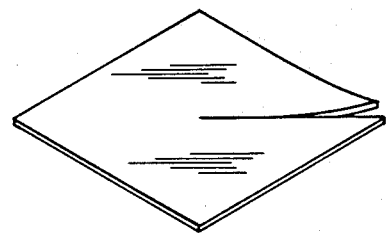
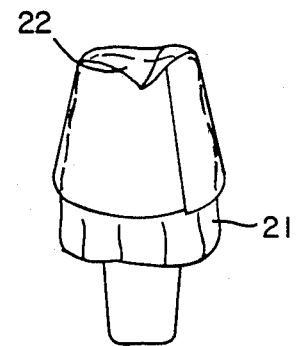
FIG. 4

SLITTED METAL FOIL FOR FORMING A DENTAL COPING AND METHOD

This invention relates to a slitted metal foil for forming a dental coping and to a method of forming a coping from a metal foil.

BACKGROUND OF INVENTION

A metal coping is used in dentistry in the construction of a dental crown and bridge. The metal coping functions as the understructure of the crown and is usually covered with a fired on coating of an acrylic or ceramic composition for the purpose of aesthetics. The metal coping supports the coating and provides the required structural strength and rigidity for the restored tooth to resist the forces of mastication.

A metal coping has recently been developed for constructing a porcelain to metal crown which can be formed without waxing, investing or casting. The coping is described in U.S. Pat. Nos. 4,459,112 and 4,492,579, and is formed from a thin metal foil of two or more layers of metal arranged in a prefolded configuration with a plurality of foldable sections. The metal foil is mounted over a die of the preferred tooth to be restored and the foldable sections are folded over in an overlapping relationship until the foil is tightly wrapped around the die. The coping is then adapted to the die preferably by swaging. Upon removal from the die, the coping is heat treated which sinters the overlapping folds to one another to form a unitary mass of substantially increased strength and rigidity relative to the metal foil in its unfolded state.

SUMMARY OF THE INVENTION

In accordance with the present invention, a thin metal foil is provided with one or more slits to permit the foil to be curled inside itself with the slitted ends overlapping in an arrangement which forms a cone-like or frusto-conical configuration. The preformed foil forms a dental coping which may then be mounted over a die of the prepared tooth to be restored and adapted to the tooth preferably by swaging. The size of the foil controls the number of overlapping layers which are formed using the curling operation of the present invention to accommodate a given size tooth. The metal foil has a composite body formed from at least two layers of precious metal with one layer composed of a low fusing temperature gold base metal composition of up to 100% gold and another layer composed of a relatively high fusing temperature metal and includes at least one slit extending from the perimeter of the foil to a location at or relatively close to the center of the foil to form slitted ends adapted to be overlaid in an arrangement for forming a coping having a substantially conical or frusto-conical shape.

A dental coping is formed in accordance with the method of the present invention from a metal foil composed of a plurality of precious metal layers comprising the steps of: making at least one slit in the foil extending from the perimeter of the foil to a location at or near the center of the foil for forming slitted ends; and overlapping the slitted ends of the foil to form a coping with a conical or frusto-conical shape.

The dental coping of the present invention comprises a metal foil formed from at least two layers of precious metal with one layer composed of a low fusing temperature gold based metal composition of up to 100% gold and another layer composed of a relatively high fusing temperature metal in an arrangement with the foil having a curled layer(s) in cross section.

OBJECTS AND BRIEF DESCRIPTION OF THE DRAWINGS

It is a principal object of the present invention to provide a metal foil for forming a dental coping particularly suited for the preparation of a ceramic-metal dental restoration.

It is a further object of the present invention to provide a method of forming a dental coping from a thin metal foil.

These and other objects of the present invention will become apparent from the following detailed description of the invention when read in conjunction with the accompanying drawings, of which:

FIG. 4 shows the foil of FIG. 3 mounted over a die of a tooth for adapting the coping to the die;

FIG. 6 shows the slitted foil of FIG. 5 folded in accordance with the present invention;

FIG. 7 shows a slitted foil of a rectangular geometry for forming a dental coping in accordance with the present invention.

DETAILED DESCRIPTION OF THE INVENTION

Referring now more particularly to the drawings in which the metal foil 10 of the present invention is shown composed of two or more layers of metal preferably laminated to form a composite structure. The number of layers is not critical to the invention, although at least two but preferably three layers is desired.

Figure 1:
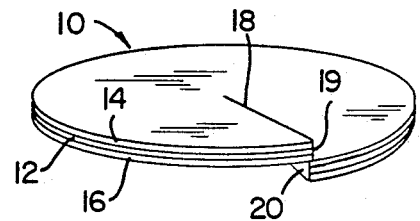
FIG. 1 is a perspective view of a slitted metal foil for forming a dental coping suited for the preparation of a ceramo-metal dental restoration.

The foil of FIG. 1 has three layers of metal with the intermediate layer 12 formed from a high fusing temperature precious metal or metal alloy composed of, e.g., palladium or platinum or a combination thereof. A high fusing temperature metal for purposes of the present invention is intended to mean a metal having a melting temperature of above about 1250° C. The layers 14 and 16 which are located on opposite sides of layer 12, should preferably also be composed of a precious metal or metal alloy having a low fusing temperature relative to the high fusing temperature precious metal layer 12. The preferred low fusing metal layer is composed of gold or a gold alloy. Although only three layers are shown, any desired number of layers may be used and preferably with each metal layer of high fusing temperature having two symmetrically disposed layers of low fusing temperature on opposite sides thereto. In a two layer arrangement, only a high and low fusing metal is required.

The metal foil 10 should be very thin generally between about only 15 to 100 microns in thickness so that the foil is easily folded in accordance with the present invention to form a coping which is readily adapted to a die of the tooth to be restored. In the unfolded state, the metal foil 10 may have any geometrical shape, although a circular shape is preferred. A rectangular shape as shown in FIG. 7 may equally be used.

Figure 2:
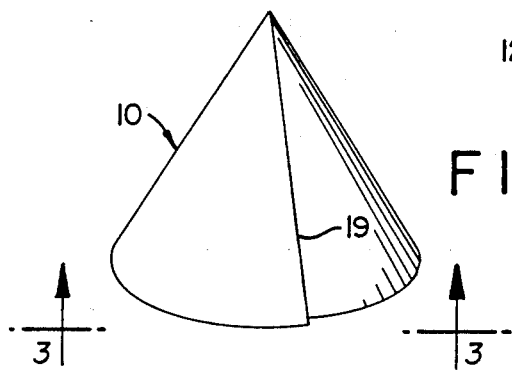
FIG. 2 shows the foil of FIG. 1 folded to form a dental coping in accordance with the method of the present invention.
Figure 3:
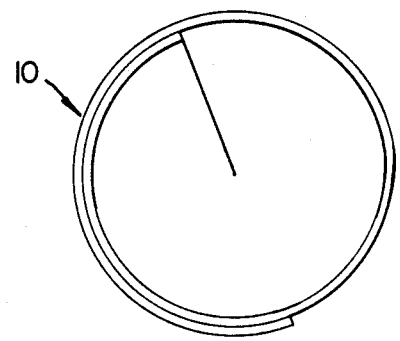
FIG. 3 is a bottom view of the folded foil taken along the lines 3—3 in FIG. 2.

A slit 18 is formed in the foil 10 either as a step in the stamping process of making the foil or simply by using shears The slit 18 should extend from the periphery of the foil 10 to a point substantially at or near the geometrical center of the foil preferably in a radial direction. The slit 18 forms two adjacent layers or slitted ends 19 and 20 which are separately held and folded over each other in an overlapping relationship. By pulling the ends 19 and 20 in opposite directions, the folded ends will curl around one another to cause the foil 10 to form a cone-like geometry as shown in FIG. 2. A bottom view of the cone shaped foil of FIG. 2 is shown in FIG. 3. The dental coping thus formed has a curled layer which in cross section forms a coil with a predetermined number of overlapping layers. The number of overlapping layers is determined by the size of the foil and how tightly the coil is wound up.

The conical shaped foil of FIG. 2 defines a preformed coping which may then be adapted to a die 21 of a tooth to be restored. It may be desirable to fold over the top or apex 22 of the cone shaped foil coping so that the folded over top 22 is mounted flush with the occlusal surface of the die 21 as shown in FIG. 4. It may also be desirable depending upon how poorly the cone shaped coping geometry conforms to the die geometry to pinch excess material to form one or more seams extending from the apex (not shown) so that the coping shape more closely conforms to the shape of the die. If the coping is properly sized for the tooth to be restored, the geometry of the cone should conform adequately to the die shape without forming any seams. After preparing and mounting the foil coping over the die, the foil is adapted to the die preferably using a conventional swager. After the coping is adapted to the die, it is heat treated before ceramic material is applied to the coping and fired to complete a dental restoration.

Figure 5:
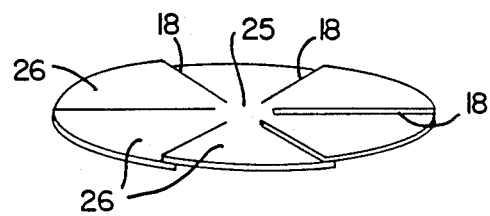
FIG. 5 shows a foil with multiple slits for forming a dental coping in accordance with the present invention.

Although only one slit 18 in the foil 10 is necessary to form a dental coping of the present invention, an arrangement with multiple slits 18 as shown in FIG. 5 may be used. In this case, it is preferred that the slits 18 extend only to a location near the center of the foil so as to leave an area 25 which may be readily flush mounted on the occlusal surface of the die without any folding. The multiple slits 18 form leaves 26 which are interleaved in an overlapping arrangement. In a manner similar to that described with reference to FIGS. 1 to 3, each of the leaves 26 is overlaid over adjacent leaves in a clockwise or counterclockwise direction until the overlapping leaves form a conical geometry with the foil having a frusto-conical geometry as shown in FIG. 6. For the multiple slit arrangement, the top area 25 lies flat without folding which provides the frusto-conical shape for the foil.

What is claimed is:

1. A metal foil having a composite body formed from at least two layers of precious metal with at least one layer composed of a low fusing temperature gold based metal composition of up to 100% gold and another layer composed of a relatively high fusing temperature metal and including at least one slit extending from the perimeter of the foil to a location at or relatively close to the center of the foil to form slitted ends adapted to be overlaid in an arrangement for forming a coping having a substantially conical or frusto-conical shape.

2. A metal foil as defined in claim 1 wherein said metal foil is composed of at least three layers with each high fusing temperature metal layer having a low fusing temperature metal layer on each side thereof.

3. A metal foil as defined in claim 2 having only one slit which extends from the perimeter of the foil to the foil center.

4. A metal foil, as defined in claim 1, wherein said foil has multiple slits which form leaves adapted to be interleaved in an overlapping arrangement.

5. A metal foil, as defined in claim 4, wherein said multiple slits extend to a location near the center of the foil so as to leave an unslitted area adapted to be mounted on the occlusal surface of a prepared tooth.

6. A method of forming a dental coping from a metal foil composed of at least two metal layers for use in a dental restoration comprising: making at least one slit in the foil extending from the perimeter of the foil to a location at or near the center of the foil for forming slitted ends and overlapping the slitted ends of the foil to form a coping with a conical or frusto-conical shape.

7. A method as defined in claim 6 wherein the foil has only one slit with the slitted ends pulled in opposite directions relative to one another so that the foil curls around in a coil like pattern.

8. A method as defined in claim 6 wherein said metal foil is circular in shape.

9. A method as defined in claim 6 wherein said metal foil is rectangular in shape.

* * * * *